(12) United States Patent
Shigematsu et al.

(10) Patent No.: US 7,573,186 B2
(45) Date of Patent: Aug. 11, 2009

(54) ELECTRODE FOR ELECTROCHEMICAL MEASUREMENT

(75) Inventors: Taishi Shigematsu, Ashigarakami-gun (JP); Miho Watanabe, Ashigarakami-gun (JP); Chikara Manabe, Ashigarakami-gun (JP); Hiroyuki Watanabe, Ashigarakami-gun (JP)

(73) Assignee: Fuji Xerox Co., Ltd., Tokyo (JP)

( * ) Notice: Subject to any disclaimer, the term of this patent is extended or adjusted under 35 U.S.C. 154(b) by 880 days.

(21) Appl. No.: 10/863,732

(22) Filed: Jun. 9, 2004

(65) Prior Publication Data

US 2008/0105544 A1    May 8, 2008

(30) Foreign Application Priority Data

Dec. 15, 2003    (JP) ............................. 2003-417035

(51) Int. Cl.
*H01J 1/02* (2006.01)
*H01B 1/00* (2006.01)
*C08F 220/04* (2006.01)

(52) U.S. Cl. ..................... 313/309; 313/311; 252/500; 524/376; 524/379

(58) Field of Classification Search ............ 204/403.14; 313/309, 311; 252/500; 524/376, 379
See application file for complete search history.

(56) References Cited

U.S. PATENT DOCUMENTS

| | | | |
|---|---|---|---|
| 5,338,430 A * | 8/1994 | Parsonage et al. ............ 204/412 |
| 6,066,448 A | 5/2000 | Wohlstadter et al. |
| 6,090,545 A | 7/2000 | Wohlstadter et al. |
| 6,140,045 A | 10/2000 | Wohlstadter et al. |
| 6,207,369 B1 | 3/2001 | Wohlstadter et al. |
| 6,464,849 B1 * | 10/2002 | Say et al. ............... 204/403.14 |
| 6,528,020 B1 * | 3/2003 | Dai et al. ...................... 422/98 |
| 6,673,533 B1 | 1/2004 | Wohlstadter et al. |
| 2001/0021534 A1 | 9/2001 | Wohlstadter et al. |
| 2002/0179434 A1 | 12/2002 | Dai et al. |
| 2003/0052585 A1 | 3/2003 | Guillorn et al. |
| 2003/0089893 A1 | 5/2003 | Niu et al. |

(Continued)

FOREIGN PATENT DOCUMENTS

JP    A 3-272449    12/1991

(Continued)

OTHER PUBLICATIONS

Joseph Wang et al.; "Carbon Nanotube/Teflon Composite Electrochemical Sensors and Biosensors"; *Analytical Chemistry*; American Chemical Society; vol. 75, No. 9; May 1, 2003; pp. 2075-2079.

(Continued)

*Primary Examiner*—Nimeshkumar D. Patel
*Assistant Examiner*—Anne M Hines
(74) *Attorney, Agent, or Firm*—Oliff & Berridge, PLC

(57) ABSTRACT

The present invention provides an electrode for electrochemical measurement including a carbon nanotube, a catalyst causing a specific chemical reaction, and an insulator in which the carbon nanotube and the catalyst are embedded, wherein a part of the catalyst is exposed at the surface of the insulator and a part of the carbon nanotube is exposed at the surface of the insulator to form an electoconductive portion, or wherein a part of the catalyst is exposed at the surface of the insulator, and a part of the carbon nanotube is electrically connected to the exposed catalyst to form an electoconductive portion.

20 Claims, 6 Drawing Sheets

U.S. PATENT DOCUMENTS

| | | | |
|---|---|---|---|
| 2003/0234428 A1* | 12/2003 | Schmid et al. | 257/369 |
| 2004/0067530 A1* | 4/2004 | Gruner | 435/7.1 |
| 2004/0086423 A1 | 5/2004 | Wohlstadter et al. | |
| 2005/0040371 A1 | 2/2005 | Watanabe et al. | |
| 2005/0053826 A1* | 3/2005 | Wang et al. | 429/44 |
| 2006/0068499 A1 | 3/2006 | Wohlstadter et al. | |
| 2006/0138394 A1 | 6/2006 | Den et al. | |
| 2006/0172340 A1 | 8/2006 | Wohlstadter et al. | |
| 2006/0249711 A1 | 11/2006 | Niu et al. | |
| 2008/0176983 A1 | 7/2008 | Niu et al. | |

FOREIGN PATENT DOCUMENTS

| | | |
|---|---|---|
| JP | A 2003-109689 | 4/2003 |
| JP | A 2003-227808 | 8/2003 |
| WO | WO 01/25474 A2 | 4/2001 |
| WO | WO 01/25474 A3 | 4/2001 |
| WO | WO 03/093169 A2 | 11/2003 |

OTHER PUBLICATIONS

Marc Delvaux et al.; "Immobilisation of glucose oxidase within metallic nanotubes arrays for application to enzyme biosensors"; *Biosensors and Bioelectronics*; Elsevier Science Publishers; vol. 18; Jul. 1, 2003; pp. 943-951.

Pons et al. "The Behavior of Electrodes," Analytical Chemistry, vol. 59, No. 24, Dec. 15, 1987, pp. 1391 A-1399 A.

Padeste et al. "Ferrocene-Avidin Conjugates for Bioelectrochemical Applications," Biosensors & Bioelectronics, vol. 15, 2000, pp. 431-438.

* cited by examiner

ELECTRODE FOR ELECTROCHEMICAL MEASUREMENT

CROSS-REFERENCE TO RELATED APPLICATION

This application claims priority under 35 USC 119 from Japanese Patent Application No. 2003-417035, the disclosure of which is incorporated by reference herein.

BACKGROUND OF THE INVENTION

1. Field of the Invention

The present invention relates to an electrode for electrochemical measurement used in sensors for detecting specific substances.

2. Description of the Related Art

Conventionally, attempts have been made to use carbon nanotubes as electronic devices because of their semiconductive characteristics.

The advantage of using carbon nanotubes as electronic devices is their extremely high conductivity. Their small diameters of 1 to 20 nm or so are also suitable to be used as devices and electrodes in micro circuits.

On the other hand, from the viewpoint of the application to the medical field, biosensors for detecting trace amounts of biological substances are being heavily studied and developed. Detecting methods in the actual use may be classified into these three methods:

(1) electrochemical method;
(2) enzymatic method; and
(3) color reaction method.

Among these, the electrochemical method is the most widespread detecting method. Substances have inherent oxidation-reduction potentials, and by applying a specific potential, electrons may be pulled out of (oxidation) or injected into (reduction) a substance. Therefore, electron transfer involved in the oxidation-reduction reactions may be measured by cyclic voltammetry or the like so as to find the amount of the target substance from the current value at a given potential.

In the electrochemical method, micro electrodes are used to improve detecting sensitivity. The micro electrodes refer to electrodes having sizes of a μm level or smaller, while the electrodes generally used for electrochemical measurement have sizes of several millimeters to several centimeters (See, for example, S. Pons and M. Fleischmann, Analytical Chemistry, 1987, vol. 59, page 1391A). Use of such micro electrodes provides the following advantages (1) to (4):

(1) contribution of charging currents causing noises may be reduced;
(2) potentials may be swept at a high speed;
(3) influence of substance dispersion may be reduced; and
(4) highly sensitive measurement may be attained.

Owing to these advantages, use of micro electrodes has been widespread in detecting trace amounts of samples by the electrochemical method, and recently, higher sensitivity is desired.

On the other hand, the enzymatic method is a method for detecting a target substance electrochemically by using electrodes having an enzyme fixed on their surfaces. Enzymes have the feature of being capable of selectively detecting the target substance at comparatively high sensitivity from a mixture because they react specifically with the target substance. So far, glucose sensors (diabetes testing), uric acid sensors (gout testing), and urea sensors (kidney function testing) are already in actual use in the medical field. However, there is a problem that the enzyme is difficult to handle because it is instable and must be stored in a special circumstance to maintain its activity.

The color reaction method is a method for detecting a biological substance by measuring the ultraviolet-visible absorption spectrum using a sample which develops color when reacted with the target substance, and by finding its absorbance. However, the detecting sensitivity in the absorbance measurement is in proportion to the light path length, whereby a large number of sample solutions are needed to enhance sensitivity. Thus, the method has a problem of inability to be applied for detecting trace amounts of samples.

Sensors utilizing the electrochemical detecting method include: sensors for detecting a specific substance by using ion sensitive field-effect transistors (See, for example, Japanese Patent Application Laid-open (JP-A) No. 03-272449); sensors for detecting hydrogen peroxide by using an electrode with ferrocene fixed on its surface (See, for example, C. Padeste et. al, "Ferrocene-avidinconjugates for bioelectochemical applications," Biosensors & Bioelectronics, 2000, volume 15, pp. 431-8); and sensors for detecting a specific substance by using a carbon nanotube as an electrode and making use of changes in electric properties of the carbon nanotube by outer stimulations (See, for example, JP-A No. 2003-227808). However, these sensors are unsatisfactory in terms of the aforementioned viewpoint, and improvements are still demanded.

SUMMARY OF THE INVENTION

The present invention has been made in view of the above circumstances and provides an electrode for electrochemical measurement capable of detecting trace amounts of a substance at high sensitivity.

A first aspect of the invention is to provide an electrode for electrochemical measurement which comprises a carbon nanotube, a catalyst causing a specific chemical reaction, and an insulator in which the carbon nanotube and the catalyst are embedded, wherein a part of the catalyst is exposed at a surface of the insulator, and a part of the carbon nanotube is exposed at the surface of the insulator to form an electoconductive portion.

A second aspect of the invention is to provide an electrode for electrochemical measurement which comprises a carbon nanotube, a catalyst causing a specific chemical reaction, and an insulator in which the carbon nanotube and the catalyst are embedded, wherein a part of the catalyst is exposed at a surface of the insulator, and a part of the carbon nanotube is electrically connected to the exposed catalyst to form an electoconductive portion.

BRIEF DESCRIPTION OF THE DRAWINGS

Preferred embodiments of the present invention will be described in detail based on the following figures, wherein:

FIGS. 1A and 1B are schematic views of an electrode for electrochemical measurement according to an embodiment of the present invention, in which FIG. 1A is a plan view and FIG. 1B is a cross sectional view;

DETAILED DESCRIPTION OF THE INVENTION

Figure 1A:
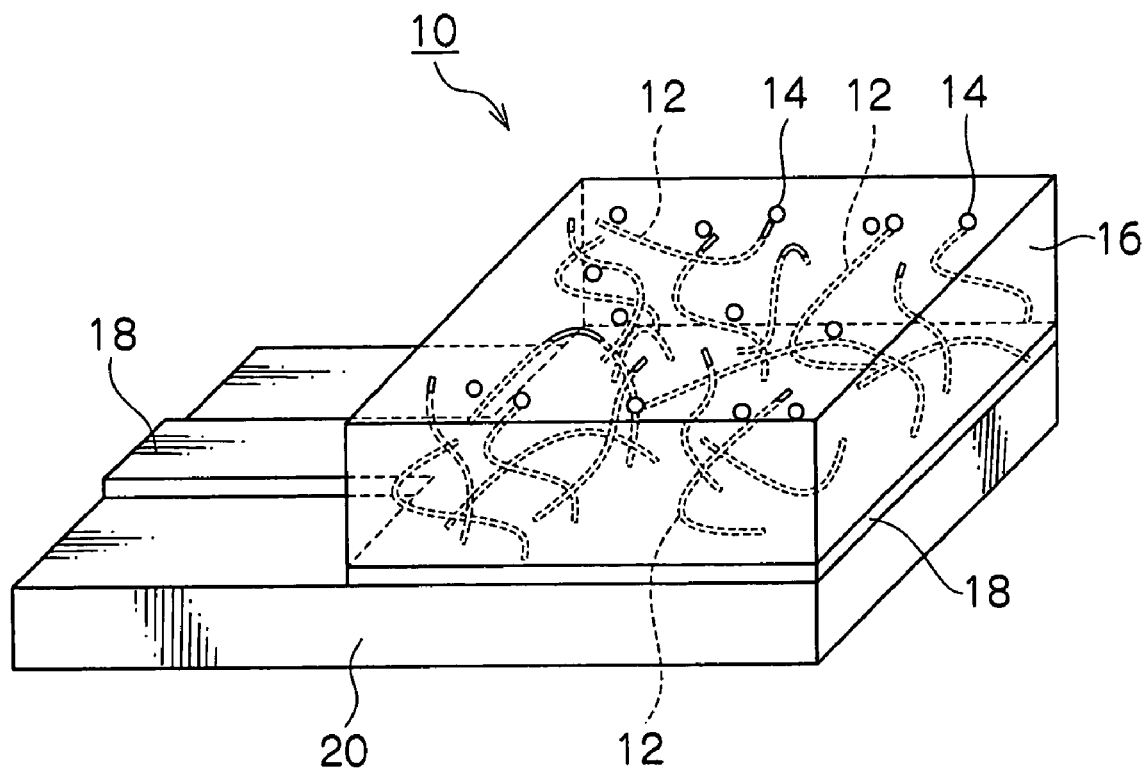

As described above, a first aspect of the invention is to provide an electrode for electrochemical measurement which comprises a carbon nanotube, a catalyst causing a specific chemical reaction, and an insulator in which the carbon nanotube and the catalyst are embedded, wherein a part of the catalyst is exposed at a surface of the insulator, and a part of the carbon nanotube is exposed at the surface of the insulator to form an electoconductive portion.

And a second aspect of the invention is to provide an electrode for electrochemical measurement which comprises a carbon nanotube, a catalyst causing a specific chemical reaction, and an insulator in which the carbon nanotube and the catalyst are embedded, wherein a part of the catalyst is exposed at a surface of the insulator, and a part of the carbon nanotube is electrically connected to the exposed catalyst to form an electoconductive portion.

In the electrodes for electrochemical measurement according to the first and second aspects of the invention, it is preferable that the carbon nanotube comprises a plurality of carbon nanotubes, the carbon nanotubes are electrically connected with each other, and a part of the plurality of the carbon nanotubes are exposed through the insulator at plural spots on the surface of the insulator to form the electoconductive portion. It is also preferable that the plurality of the carbon nanotubes are electrically connected with each other by chemical bonding to thereby form a network structure.

In the electrodes for electrochemical measurement according to the first and second aspects of the invention, it is preferable that the catalyst is at least one selected from the group consisting of metal, metal oxide, protein, and carbon pieces carrying any of these substances. The metal is preferably at least one selected from the group consisting of platinum, silver, gold, iron, copper, and silicon. The metal oxide is preferably at least one selected from the group consisting of platinum black, enzymes, iron oxide, cobalt oxide, titanium oxide, tin oxide, indium oxide, gallium oxide, silicon oxide, silicon, zinc oxide, ruthenium oxide, hafnium oxide, and tungsten oxide. The protein is preferably at least one selected from various enzymes.

In the electrodes for electrochemical measurement according to the first and second aspects of the invention, it is preferable that the insulator has a volume resistivity value in a range of $1 \times 10^5$ to $1 \times 10^{10}$ Ωcm. It is also preferable that a material for the insulator is selected from the group consisting of polyether ketone, polyketone, polyimide, polycarbonate, polystyrene, and polyethylene.

Hereinafter, the present invention will be explained with reference to the drawings. The members having substantially the same functions will be referred to with the same reference numerals throughout the drawings.

Figure 1B:
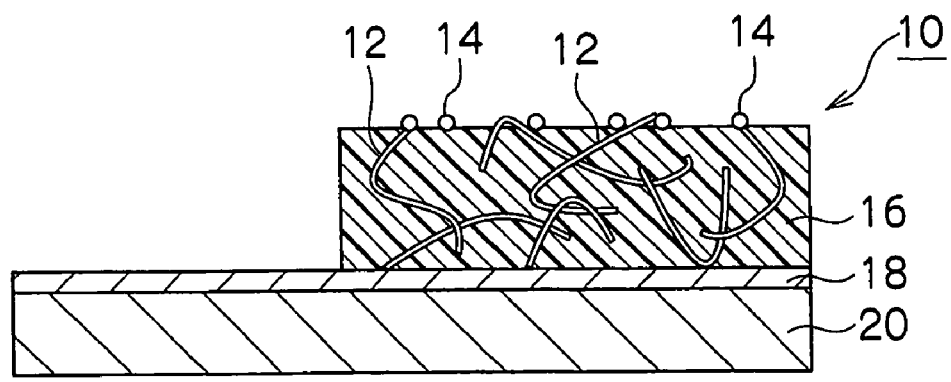

FIG. 1 is a schematic view of an electrode for electrochemical measurement according to an embodiment of the invention; FIG. 1A is a plan view and FIG. 1B is a cross sectional view.

The electrode for electrochemical measurement 10 of this embodiment comprises an insulator 16 in which plural carbon nanotubes 12 and a catalyst 14 causing a specific chemical reaction are embedded, and the electrode 10 is provided on a substrate 20 having a conductor for extracting currents 18. The plural carbon nanotubes 12 are embedded in the insulator 16 in such a state that they are electrically connected with each other. Incidentally, the substrate 20 is not an essential component. For example, a configuration may be possible in which the insulator 16 is arranged as an electrode on a film-like conductor for extracting currents.

The catalyst 14 is exposed at the surface of the insulator 16, and a part of the plural carbon nanotubes 12 are also exposed at the surface of the insulator 16 through the insulator 16 so as to form an electoconductive portion 22. In other words, the plural carbon nanotubes 12 are exposed at plural spots in a mutually electrically isolated state. Consequently, the catalyst 14 acts as an electrode portion (chemical reactive region), the carbon nanotubes 12 serves as conducting wires, and the insulator 16 contributes as an insulating film. The conductor for extracting currents 18 is electrically connected with the part of the plural carbon nanotubes 12.

Figure 2:
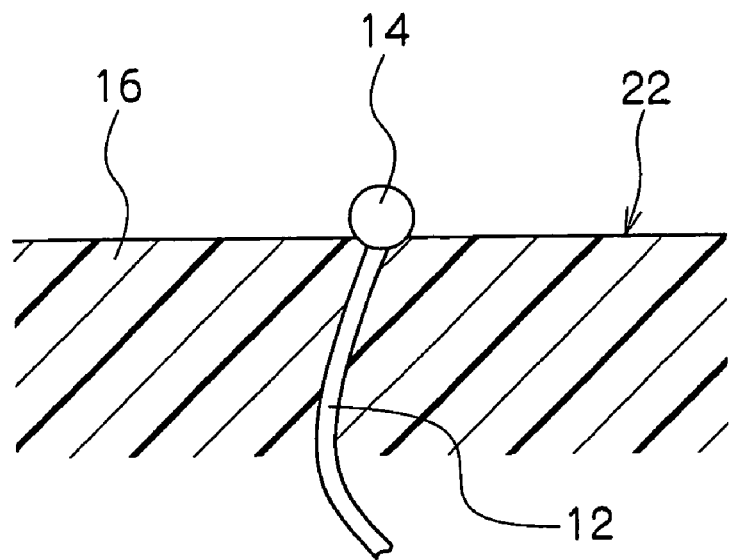
FIG. 2 is a schematic cross sectional view showing an electoconductive portion of an electrode for electrochemical measurement according to an embodiment of the invention.
Figure 3:
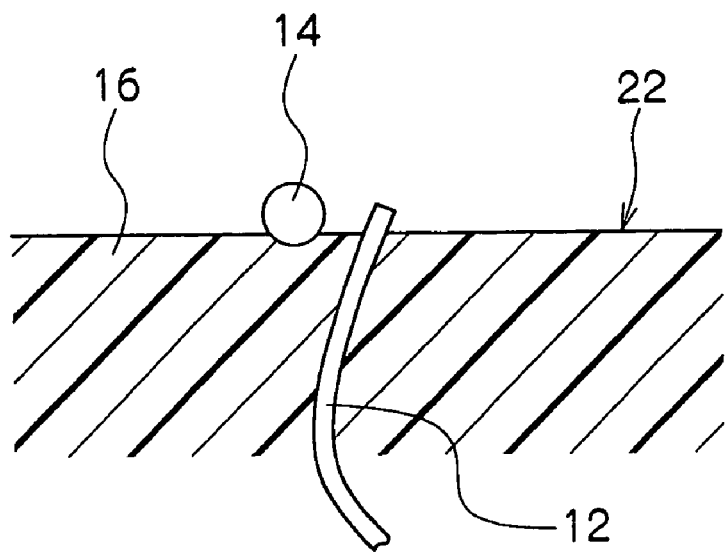
FIG. 3 is another schematic cross sectional view showing an electoconductive portion of an electrode for electrochemical measurement according to an embodiment of the invention.

The electoconductive portion 22 may comprise two modes: in a first mode as shown in FIG. 2, a part of the carbon nanotube 12 are electrically connected with the catalyst 14 exposed at the surface of the insulator 16; in a second mode as shown in FIG. 3, the catalyst 14 and the carbon nanotube 12 are individually exposed at the surface of the insulator 16. For the electoconductive portion 22, the first and second modes are both possible, and either one of the two modes may be employed.

In the first mode, migration of electrons involved in the chemical reaction caused by the catalyst 14 is detected by the carbon nanotube 12 directly connected with the catalyst 14. On the other hand, in the second mode, migration of electrons involved in the chemical reaction caused by the catalyst 14 is detected by the carbon nanotubes 12 exposed in the vicinity of the catalyst 14.

In either mode, the carbon nanotube 12 detects, in parallel, movements of electrons involved in the chemical reaction caused by the catalyst 14 at plural spots in the electoconductive portion 22, and currents are extracted into the conductor for extracting currents 18 through the carbon nanotube 12 electrically connected with each other in the insulator 16.

Since the plural carbon nanotubes 12 are embedded in the insulator 16 in a mutually electrically connected condition, the currents detected at the electoconductive portion 22 may be extracted into the conductor for extracting currents 18, without causing almost any loss.

The electrode for electrochemical measurement of the present invention may have any shape such as a rectangular parallelepiped, a cylinder, or the like.

In the electrode for electrochemical measurement of this embodiment, the chemical reaction caused by the catalyst 14 acting as the electrode portion is detected by the carbon nanotube 12 having a significantly good conductive efficiency, thereby making it possible to detect trace amounts of a substance at high sensitivity by means of a specific chemical reaction effected with the catalyst 14. Furthermore, the electrode can be stably handled in the air because the electrode is composed of the catalyst 14, the carbon nanotubes 12, and the insulator 16.

Since the chemical reaction caused by the catalyst 14 acting as the electrode portion is detected at plural spots, in parallel, by the carbon nanotube 12, detecting sensitivity can be improved.

Generally, detection of the substance using the electrochemical method has increased sensitivity with decreasing electrode sizes, whereby detecting sensitivity may be improved by reducing the size of the catalyst 14 that acts as the electrode portion.

In this embodiment, in-parallel configured electric connection is exemplified in which plural carbon nanotubes are used, however, it is also possible to use a single carbon nanotube to compose the electrode. In such a case, only a part of the single carbon nanotube 12 is exposed at the surface of the insulator 16 to render the substantial electrode portion (electoconductive portion) to have a micro size, and accordingly, a high-sensitive sensor may be achieved when it is used as a sensor.

Hereinafter, respective materials used in the present invention will be described in more detail. In the following description, reference numerals are omitted.

Carbon Nanotube

The carbon nanotubes may be single-wall carbon nanotubes or multi-wall carbon nanotubes. Which of the two type carbon nanotubes should be used or if they are used in combination may be selected appropriately. It is also possible to use, as carbon nanotubes, those not having an exact tube shape such as a carbon nanohorn which is one of variations of the single-wall carbon nanotube (a horn-type whose diameter gradually becomes larger from one end to the other), a carbon nanocoil (a coil-type having a spiral shape as a whole), a carbon nanobead (a type having a tube at the center and the tube extends through an entire spherical bead composed of amorphous carbon or the like), a cup-stacked type, or a carbon nanotube coated with a carbon nanohorn or amorphous carbon.

Additional kinds of tubes which may be used as carbon nanotubes, such as metal-containing nanotubes containing metal or the like, peapod nanotubes containing fullerene or metal-containing fullerene, and other carbon nanotubes containing any substance.

As described supra, in addition to ordinary carbon nanotubes, any types of carbon nanotubes may be used that include those of variously modified, without any problem, in view of their reactivity. Accordingly, the "carbon nanotube" as used herein encompasses all of these types.

In case where the carbon nanotubes are electrically connected with each other by the mutual contact, contacting condition, moving mechanical and electric strength may be altered by bending of the electrode and other operations, thereby failing to sufficiently exert the performances. Further, increased electric conductivity requires an increased amount of carbon nanotubes to be introduced (to be embedded), which may inevitably decrease the content of insulator, thereby impairing mechanical strength of the electrode itself.

Therefore, the carbon nanotubes preferably comprise a network structure in which they are electrically connected with each other by chemical bonding, from the viewpoint of improving the electric conductivity and mechanical strength of the carbon nanotubes themselves as well as electrode intensity. One specific example is a cross-linked carbon nanotube structure in which functional groups present in plural carbon nanotubes are chemically bonded with each other to thus form a network structure.

The cross-linked carbon nanotube structure has cross-linked moieties formed by chemically linking the functional groups of the plural carbon nanotubes, and the cross-linked moieties preferably have either a first structure in which plural functional groups are cross-linked with each other using a cross-linking agent, or a second structure in which plural functional groups are linked chemically with each other.

The first structure is a cross-linked structure in which functional groups remaining after the cross-linking reaction are linked with each other via a linking group of the cross-linking agent which are remained after the cross-linking reaction.

When the cross-linking agent has an ability of causing a polymerization reaction between the groups contained therein (self polymerizability), the structure may have the condition in which the linking group of two or more cross-linking agents are linked, substantially decreasing density of the carbon nanotubes in the cross-linked carbon nanotube structure. As a result, sufficient electric conductivity or mechanical strength of the electrode may not be obtained.

On the other hand, when the cross-linking agent has non-self polymerizability, spacing between the carbon nanotubes may be controlled to meet a size of a residue of the used cross-linking agent, whereby a desired carbon nanotube network structure can be attained at high reproducibility. Furthermore, a reduced size of the residue of the cross-linking agent enables spacing between the carbon nanotubes to adapt the conditions where the carbon nanotubes have close characteristics both electrically and physically. Furthermore, the carbon nanotubes designed as above may be embedded densely in the structure.

Therefore, if the cross-linking agent has the ability of effecting non-self polymerization, the cross-linked carbon nanotube structure can acquire excellent electric properties or mechanical strength. As used herein, "self polymerizability" indicates that the cross-linking agents can cause a polymerization reaction in the presence of water and other ingredients or in the absence of other ingredients, while "non-self polymerizability" indicates the absence of such properties.

It is to be noted that if the cross-linking agent having non-self polymerizability is selected, the cross-linked moieties where the carbon nanotubes are cross-linked with each other may have the same cross-linking structure. The linking group has preferably a skeleton of hydrocarbon having a carbon number preferably of 2 to 10. A decreased carbon number can shorten a length of the cross-linked moieties, so that the carbon nanotubes may be arranged closely to each other at a space that is shorter than the length of the carbon nanotubes themselves, and hence, a desired cross-linked carbon nanotube structure can be obtained that has a network structure substantially composed of carbon nanotubes alone.

In the first structure, examples of the functional group include —OH, —COOH, —COOR (R is a substituted or unsubstituted hydrocarbon group), —COX (X is a halogen atom), —NH$_2$ or —NCO, and at least one group selected from the groups listed above can be preferably selected. In that case, a substance capable of a cross-linking reaction with the selected functional group may be selected for use as the cross-linking agent.

Preferable cross-linking agents include: polyols, polyamines, polycarboxylic acids, polycarboxylic esters, polycarboxylic halides, polycarbodiimides, and polyisocyanates. It is preferable to select at least one cross-linking agent from the above listed, and in that case, a substance capable of cross-linking with the selected cross-linking agent is selected as a candidate having the functional group.

It is preferable to select a pair of at least one functional group and at least one cross-linking agent from the viewpoint of likability of causing a cross-linking reaction with each other.

In the first structure, a particularly preferable functional group is —COOR (R is a substituted or unsubstituted hydroxide carbon group). It is relatively easy to introduce carboxyl groups into the carbon nanotubes, and a resultant substance (carbon nanotube carboxylic acid) has excellent reactivity, whereby it is readily carried out to esterify the substance to have a functional group of —COOR (R is a substituted or unsubstituted hydrocarbon group). This functional group is susceptible to a cross-linking reaction, and therefore, the group is suitable for formation of a coating film.

One of the cross-linking agents having such a functional group is polyols. Polyols are cured when reacted with a compound having —COOR (R is a substituted or unsubstituted hydrocarbon group) to readily form a rigid cross-linking structure. Among polyols, glycerine and ethylene glycol are preferable due to not only excellent reactivity with the functional group, but also high biodegradability themselves, without causing much hazard onto the environment.

In the first structure, the cross-linked moieties have —COOR (R is a substituted or unsubstituted hydrocarbon group) as the functional group. When ethylene glycol is used as the cross-linking agent, the cross-linked moieties have the chemical structure —COO(CH$_2$)$_2$OCO—, whereas when glycerine is used as the cross-linking agent, if two OH groups are involved in cross-linking, the cross-linked moieties have the chemical structure —COOCH$_2$CHOHCH$_2$OCO— or —COOCH$_2$CH(OCO—)CH$_2$OH; and if three OH groups are involved in cross-linking, the cross-linked moieties have the chemical structure —COOCH$_2$CH(OCO—)CH$_2$OCO—. The cross-linked moieties may have any one of these four chemical structures.

On the other hand, the second structure is formed by chemically linking the functional groups of the plural carbon nanotubes. The reaction to trigger this chemical linkage is preferably any of dehydrative condensation, substitution reaction, addition reaction, and oxidation reaction.

The cross-linked carbon nanotube structure having the second structure is a network structure composed of the cross-linked moieties formed by chemically linking the functional groups which bonds the carbon nanotubes with each other. Therefore, the size of the cross-linked moieties for connecting the carbon nanotubes become uniform depending on the functional groups to be linked. Since the carbon nanotubes have an extremely stable chemical structure, the functional groups other than those involved in desired modification are unlikely to be linked. Thus, when these functional groups are allowed to chemically link with each other, the cross-linked moieties can be designed into a intended structure, thereby achieving a homogeneous cross-linked carbon nanotube structure.

Since the second structure is formed by chemically linking between the functional groups, as compared with the case of cross-linking the functional groups using a cross-linking agent, the length of the cross-linked moieties between the carbon nanotubes can be reduced. As a result, a dense cross-linked carbon nanotube structure is attained, thereby providing augmented effects that are inherent in carbon nanotubes.

In the second structure, it is preferable to select, as the chemically linking between the functional groups, one of —COOCO—, —O—, —NHCO—, —COO—, and —NCH— in a condensation reaction; to select one of —NH—, —S—, and —O— in a substitution reaction; to select —NHCOO— in an addition reaction; and to select —S—S— in an oxidation reaction.

The functional groups to be connected to the carbon nanotubes before allowing the reaction include: —OH, —COOH, —COOR (R is a substituted or unsubstituted hydrocarbon group), —X, —COX (X is a halogen atom), —SH, —CHO, —OSO$_2$CH$_3$, —OSO$_2$(C$_6$H$_4$)CH$_3$—NH$_2$, and —NCO. It is preferable to select at least one group from these functional groups.

Among these, —COOH is a particularly suitable functional group. It is relatively easy to introduce carboxyl groups into the carbon nanotubes. Moreover, the resultant substance (carbon nanotube carboxylic acid) has excellent reactivities, and can easily cause a condensation reaction by making use of a dehydrative condensation agent such as N-ethyl-N'-(3-dimethylaminopropyl) carbodiimide, which is suitable for formation of a coating film.

As described above, the cross-linked carbon nanotube structure having the cross-linked moieties, having either the first structure or the second structure, form a network structure in which plural carbon nanotubes create a network via plural cross-linked moieties. Therefore, unlike the condition where carbon nanotubes are accidentally in contact with each other, i.e., substantially isolated from each other, advantageous characteristics of the carbon nanotubes can be stably exhibited.

Catalyst

The catalyst is preferably composed of fine particles or small pieces. Since a decreased size of the catalyst acting as the electrode portion improves detecting sensitivity as mentioned above, it is preferable that the catalyst has an average diameter of 1 nm to 100 μm, more preferably 1 nm to 10 μm, and still more preferably 1 nm to 1 μm.

Preferable examples of the catalyst include: metal, metal oxide, protein, and carbon pieces carrying any of these substances. Examples of the metal include: platinum, silver, gold, iron, copper, and silicon. Examples of the metal oxide include: platinum black, enzyme, iron oxide, cobalt oxide, titanium oxide, tin oxide, indium oxide, gallium oxide, silicon oxide, silicon, zinc oxide, ruthenium oxide, hafnium oxide, and tungsten oxide. Examples of the protein include various enzymes. These substances may be used alone or in combination of two or more kinds thereof, and it is possible to select any material capable of causing a chemical reaction with the substance to be detected.

Insulator

As a material for the insulator, any nonconductive material may be used without any problem, irrespective of whether it is organic or inorganic. As used herein, the nonconductive material does not necessarily mean an absolutely insulating material, but may be an ordinarily used semiconductive material. The insulator preferably has a volume resistivity value in a range of $1 \times 10^5$ to $1 \times 10^{10}$ Ωcm.

The material for the insulator is preferably a resin material from the viewpoint of molding property, processability, and precision. Use of the resin material makes it possible to form a nonconductive substrate, with ease and high precision, by conventional well-known methods such as layer formation by injection molding or coating/drying.

From the viewpoints of not only non-conductivity but also outer air shielding function and mechanically protective function, specific examples of the material usable as the insulator include: inorganic materials such as silicon oxide, silicon nitride, silicon oxide nitride, titanium oxide, niobium oxide, lithium niobate, strontium titanium, and diamond; various resin materials such as epoxy resin, polyimide, polyamide, polyamide-imide, polyethylene, polypropylene, polyvinyl chloride, polyvinylidene chloride, acrylic resin, polycarbonate resin, fluororesin, amide resin, polyethylene terephthalate, polyurethane, polystyrene, polyacetal, silicone resin, Teflon (a registered trade mark) resin, polyether ketone, and polyketone; and other organic materials.

Among these, polyether ketone, polyketone, polyimide, polycarbonate, polystyrene, and polyethylene are preferable.

The insulator may be chemically bonded with the carbon nanotubes. In case where carbon nanotubes having a significantly good conductive efficiency are embedded in the insulator in the state of being chemically bonded with the insulator, a degree of bonding between the carbon nanotubes and the insulator is increased, thereby suppressing the carbon nanotubes to move inside the insulator. This enables enhanced detection of trace amounts of the substance, and also broadens the potential window when measurement is carried out using a liquid.

Method for Manufacturing Electrode for Electrochemical Measurement of the Invention The electrode for electrochemical measurement of the invention may be manufactured, for example, in the following manner. First, the insulating material is dissolved in a solvent to prepare a solution. Carbon nanotubes and the catalyst are dispersed into this solution. The mixed solution thus prepared is coated on the substrate after the substrate is covered with the conductor for extracting currents, after which the solvent is evaporated off to thereby obtain an electrode. As a result, an electrode having the catalyst and carbon nanotubes exposed at the surface of the insulator to form the electoconductive portion can be produced.

There may arise a case where the catalyst having a large specific gravity is precipitated in the solution and eventually agglomerates at the lower portion of the electrode. In such a case, the electrode is formed by being coated on the substrate, and then removed from the substrate so as to utilize the lower portion (the portion to abut the substrate) as the electoconductive portion.

A carbon nanotube dispersion is prepared and coated on the substrate after the substrate is covered with the conductor for extracting currents. Another dispersion containing the insulator material and the catalyst is coated over the carbon nanotubes, after which the solvent is evaporated off. Then, one end of the obtained structure is cut off so as to expose the catalyst and the carbon nanotubes at the cut surface. As a result, an electrode utilizing the cut surface as the electoconductive portion is produced.

On the other hand, the electric connection between the carbon nanotubes and the catalyst may be established by two methods. A first method is to add the catalyst to the carbon nanotube dispersion, thoroughly mixed using a mortar or a ball mill, and then coating is applied to thus form an electrode. The second method is employed as follows. First, the carbon nanotubes are dispersed in a solution containing the insulator material, followed by coating of the resulting solution to cover an entire conductor for extracting currents, after which the solvent is evaporated off. Then, one end of the obtained structure is cut off so as to expose the carbon nanotubes. Thereafter, the catalyst is plated on the electrode surface by electrolytic plating or the like, to thus secure the catalyst to exist at the surface of the exposed carbon nanotubes.

The carbon nanotubes present in the electrode as prepared above are merely in contact with each other in the insulator, contacting condition, fluctuating mechanical and electric strength may be altered by bending of the electrode and other operations, thereby failing to sufficiently exert the performances. Further, increased electric conductivity requires an increased amount of carbon nanotubes to be introduced (to be embedded), which may decrease the content of insulator, thereby impairing mechanical strength of the electrode itself.

Therefore, it is preferable to use the aforementioned cross-linked carbon nanotube structure. For example, the carbon nanotube structure may be impregnated with a solution containing the insulator material and the catalyst so as to prepare an electrode that contains carbon nanotubes electrically bonded with each other to thereby form the network structure by chemical linking.

The obtained electrode may be patterned into a desired pattern. In this stage, the electrode structure itself is already stable, whereby the patterning under these conditions can provide a desired pattern without causing inconvenience such as scattering of the carbon nanotubes during the patterning process.

This patterning process comprises two types A and B as described below.

Type A comprises: applying dry etching onto the electrode in the region, other than an intended pattern on the substrate surface, so as to remove electrodes present in the region, thereby to accomplish patterning of the electrode into the desired pattern.

The operation of patterning the electrode into a desired pattern can be divided into two processes: a mask forming process for providing a mask layer (preferably a resin layer such as a photoresist or a metal mask) onto the electrode in the region of the desired pattern; and a removal process for removing electrodes exposed in the region other than the intended region by carrying out dry etching (preferably applying radicals of oxygen molecules. The radicals of oxygen molecules may be generated by irradiating ultraviolet rays to the oxygen molecules) to the side of the substrate where the electrode and the mask layer are layered. In such a case, when the mask layer formed during the process is a resin layer such as the photoresist, the removal process is followed by a resin layer eliminating process for eliminating the resin layer, such that the patterned electrode can be exposed.

In type A, the operation of pattering an electrode into a desired pattern may be done by selectively irradiating gas molecule ions as ion beams to the electrode at the region, other than the intended pattern, to thereby remove electrodes present in the region.

Type B comprises: a printing process comprising preparing a solution by dispersing carbon nanotubes into glycerine or the like and adding a dehydration catalyst such as sulfuric acid (referred to as "carbon nanotube dispersion"); preparing a gel by dispersing carbon nanotubes into a gelled polymer (composition) and adding the dehydration catalyst such as sulfuric acid (referred to as "carbon nanotube dispersed gel"); printing into a desired pattern and a thermosetting process for thermosetting the carbon nanotube dispersion or the carbon nanotube dispersed gel.

Either type of A or B may be used for carrying out patterning.

The electrode for electrochemical measurement of the invention has been explained with reference to preferable examples, however, the invention is not limited thereto, and any of the conventionally well-known structures may be used by modifying it and/or being added insofar as it has the structure of the present invention.

EXAMPLES

The present invention will now be explained in more detail by the following examples; however, the invention is not limited to these examples.

Example 1

Carbon nanotubes modified with carboxylic acid are synthesized in the following manner. 30 mg of multi-wall carbon nanotube (MWCNT) powder (purity: 90%, average diameter: 30 nm, average length: 3 μm, manufactured by Science Laboratory) is added to 20 ml of concentrated nitrate (a 60% by mass aqueous solution, manufactured by Kanto Kagaku), and refluxed for 20 hours at 120° C. to thereby synthesize carbon nanotube carboxylic acid. After cooled down to room temperature, the resultant solution is centrifuged at 5,000 rpm for 15 minutes so as to separate a supernatant from a precipitate. The collected precipitate is dispersed in 10 ml of pure water, and subjected to another centrifugation at 5,000 rpm for 15 minutes so as to further separate the supernatant from the precipitate (this is the completion of one-time washing operation). This washing operation is repeated additional five times and the precipitate is finally collected as carbon nanotubes that are modified with carboxylic acid.

0.02 g of the collected carbon nanotubes modified with carboxylic acid is mixed with 1 ml of glycerine (manufactured by Kanto Kagaku), 0.2 g of platinum black (average diameter: 10 μm, manufactured by Wako Pure Chemical Industries, Ltd.) as catalyst for measurement, and 10 μl of concentrated sulfuric acid (a 98% by mass aqueous solution, manufactured by Kanto Kagaku). 1 ml of this mixture is added dropwise to aluminum foil, and heated for 15 minutes at 190° C. After it is confirmed to be cured, the mixture is further heated for 30 minutes at 280° C. As a result, an electrode is prepared in which carbon nanotubes and platinum black are dispersed. This electrode has an electoconductive portion where a part of the carbon nanotubes and platinum black are exposed. The part of the carbon nanotubes are in contact with the aluminum foil serving as the conductor for extracting currents. The volume resistivity value of polyether ketone obtained from the glycerine alone is $1 \times 10^8$ Ωcm.

Figure 4:
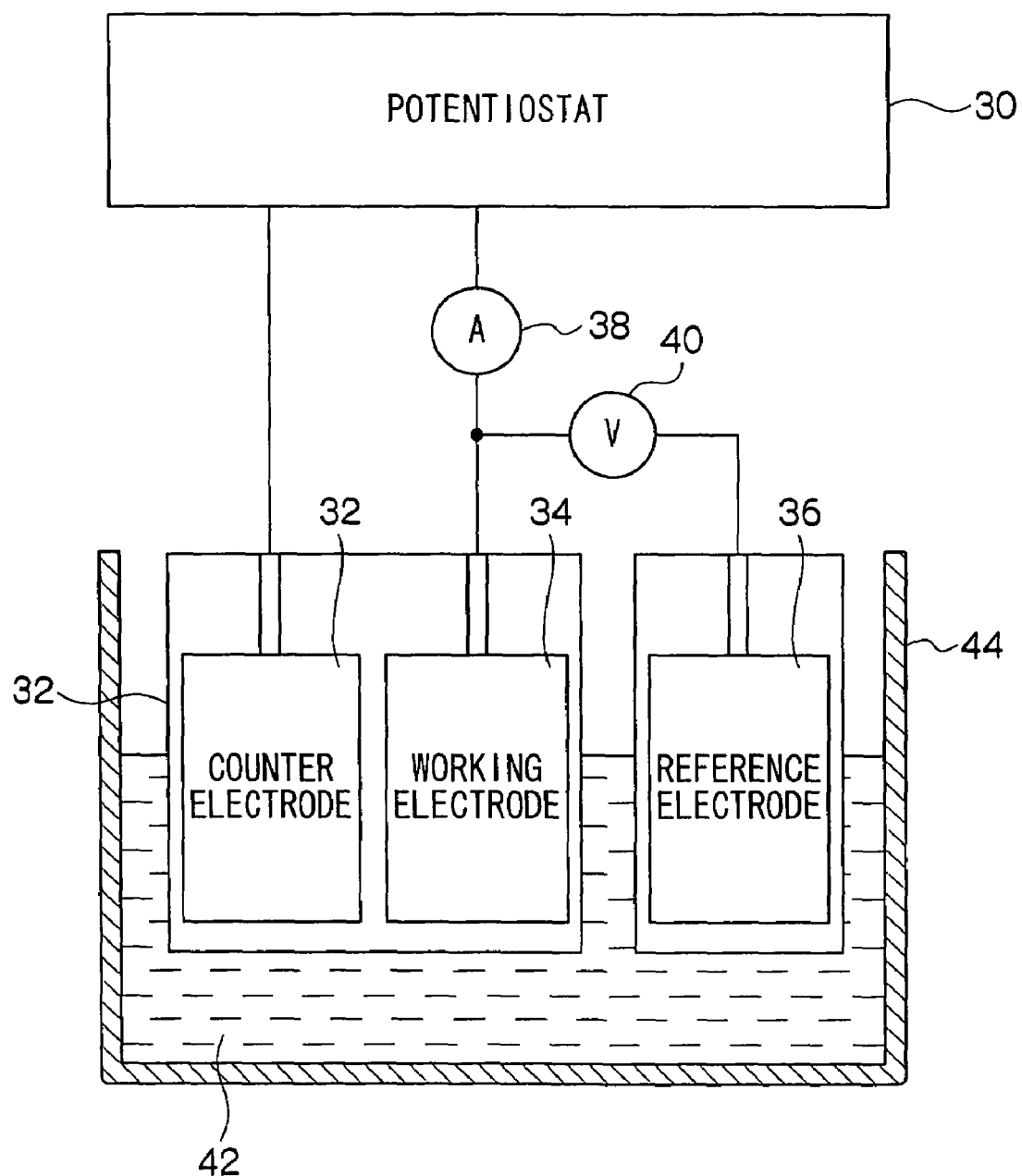
FIG. 4 is a schematic representation showing a detecting device used in Examples.

The thus prepared electrode is placed in a detecting device having the structure shown in FIG. 4 to carry out detection of hydrogen peroxide. In more detail, the prepared electrode is cut into an arbitrary shape with scissors and arranged as a working electrode and a counter electrode. An Ag/AgCl electrode is further arranged as the reference electrode. As the electrolyte, 0.1 M aqueous solution of potassium chloride (manufactured by Wako Pure Chemical Industries, Ltd.) is used. By using these electrodes, the cyclic voltammetry of hydrogen peroxide is performed, with adjusting its concentrations to 0 pM, 1 pM ($=10^{-12}$ M), 10 pM, and 100 pM. The results of measurement are shown in FIG. 5.

Figure 5:
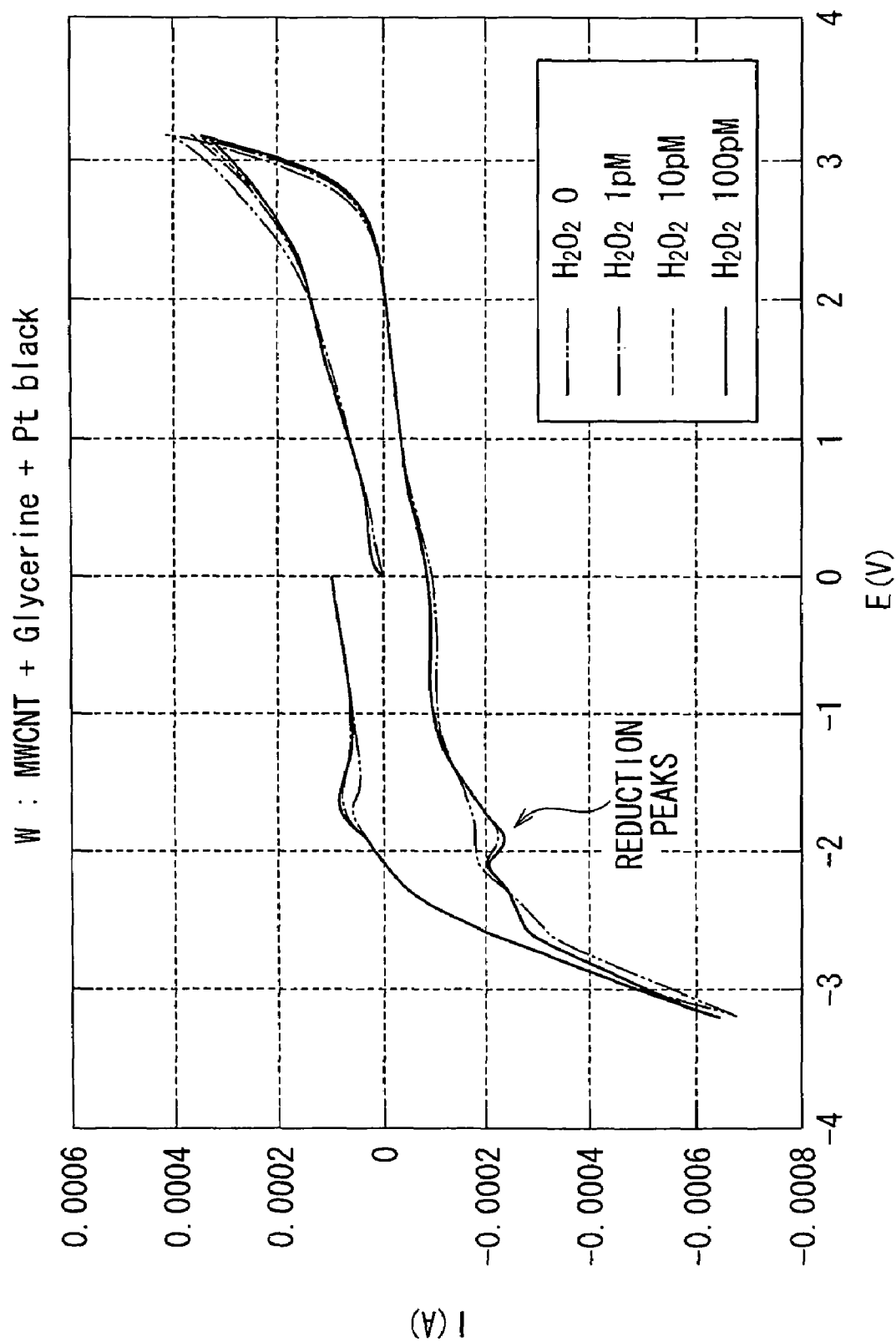
FIG. 5 is a cyclic voltammogram of hydrogen peroxide measured at respective concentrations obtained in Example 1.
Figure 6:
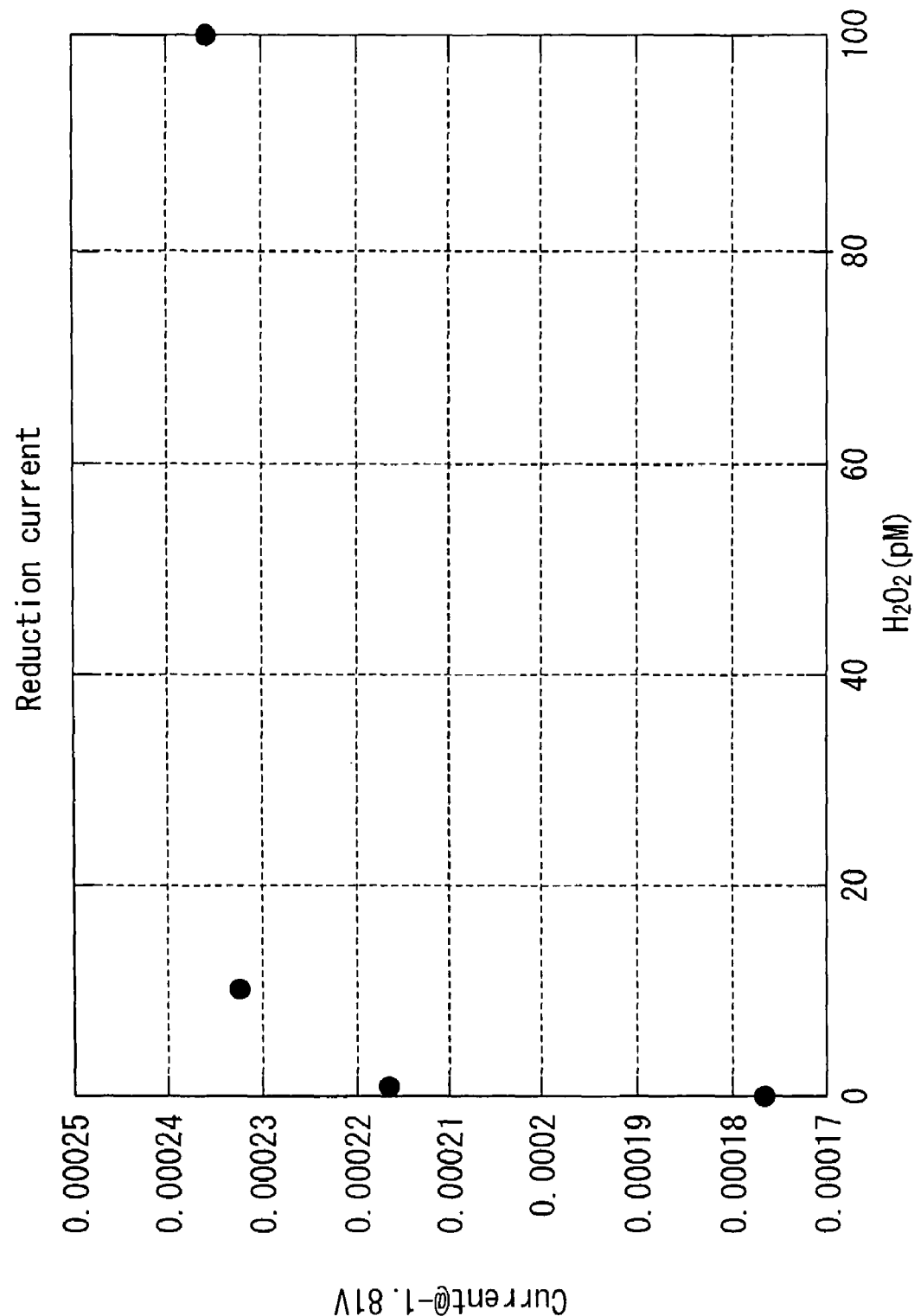
FIG. 6 is a graph showing a relation between current values and concentrations of hydrogen peroxide measured at a reduction peak obtained in Example 1.

As seen from FIG. 5, reduction peaks of the hydrogen peroxides are observed in the vicinity of −1.8 V. The current values of the reduction peaks are plotted with respect to the concentrations of the hydrogen peroxides to thereby obtain FIG. 6. It is revealed that hydrogen peroxide having a concentration of 1 pM can be detected. The obtained results also reveal that electrolysis of a solvent does not occur even if potential swept is conducted in a range of +3.2 V to −3.2 V, thus indicating a wide potential window of 6.4 V or higher.

As shown in FIG. 4, the detecting device is composed of a potentiostat 30, a counter electrode 32 connected to the potentiostat 30, a working electrode 34, and a reference electrode 36. The working electrode 34 is connected to the potentiostat 30 via an ammeter 38, and the working electrode 34 is connected with the reference electrode 36 via a voltmeter 40. In the figure, the reference numeral 42 represents an electrolytic aqueous solution of hydrogen peroxide, and the reference numeral 44 represents a container.

Example 2

Figure 7:
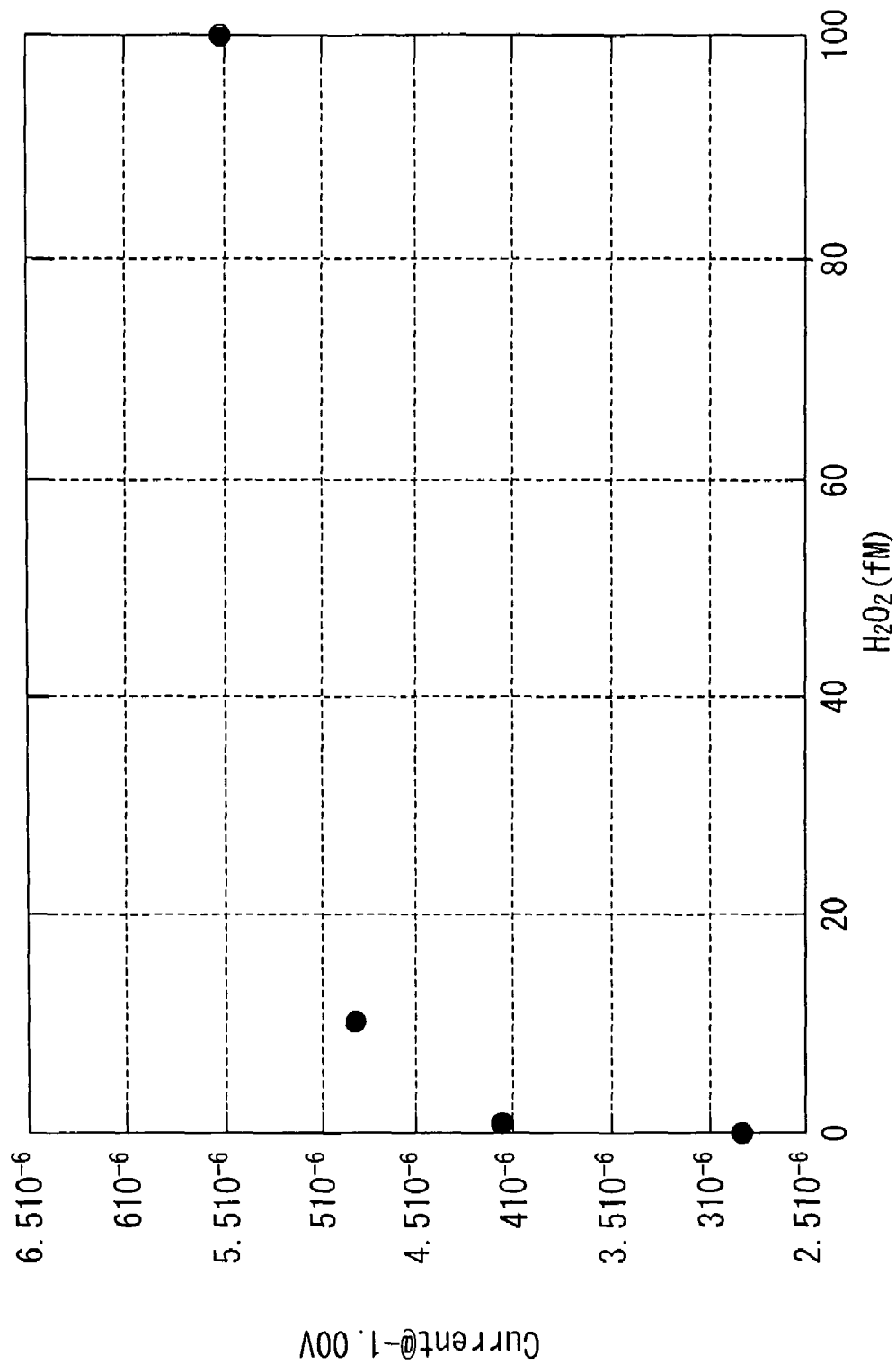
FIG. 7 is a graph showing a relation between current values and concentrations of hydrogen peroxide measured at a reduction peak obtained in Example 2.

In the same manner as in Example 1, the cyclic voltammetry of hydrogen peroxide is carried out with adjusting its concentrations to 0 fM, 1 fM ($=10^{-15}$ M), 10 fM, and 100 fM. The current values at the reduction peaks of hydrogen peroxide are plotted with respect to the respective concentrations, and the results are shown in FIG. 7. The results confirm that hydrogen peroxide having concentrations as low as 1 fM can be detected.

Comparative Example 1

Using platinum electrodes (surface area: 10 mm×30 mm, thickness: 100μ or so, and a specimen is made in contact with a surface area only) generally used for electrochemical measurement as the working electrode and the counter electrode, detection of hydrogen peroxide is carried out. In that case, only the working electrode is electrolytically plated with platinum black at an entire surface. As the reference electrode, an Ag/AgCl electrode is arranged. As the electrolyte, a 0.1 M aqueous solution of potassium chloride (manufactured by Wako Pure Chemical Industries, Ltd.) is used. With these electrodes, hydrogen peroxide having a concentration as low as 1 μM is detected, however, it is impossible to detect hydrogen peroxide having the concentration below this value.

As detailed above, the present invention provides an electrode for electrochemical measurement capable of detecting trace amounts of a substance at high sensitivity.

What is claimed is:

1. An electrode for electrochemical measurement comprising a plurality of carbon nanotubes, a catalyst causing a specific chemical reaction, and an insulator in which the carbon nanotubes and the catalyst are embedded, wherein
    the carbon nanotubes are electrically connected with each other by chemical bonding to thereby form a network structure, a part of the catalyst is exposed at a surface of the insulator, and a part of the plurality of the carbon nanotubes are exposed at the surface of the insulator to form an electroconductive portion, and
    the carbon nanotubes are cross-linked with a cross-linking agent having non-self polymerizability.

2. The electrode for electrochemical measurement of claim 1, wherein a part of the plurality of the carbon nanotubes are exposed through the insulator at plural spots on the surface of the insulator to form the electroconductive portion.

3. The electrode for electrochemical measurement of claim 1, wherein the catalyst is at least one selected from the group consisting of metal, metal oxide, protein, and carbon pieces carrying any of these substances.

4. The electrode for electrochemical measurement of claim 3, wherein the catalyst is a metal and the metal is at least one selected from the group consisting of platinum, silver, gold, iron, copper, and silicon.

5. The electrode for electrochemical measurement of claim 3, wherein the catalyst is a metal oxide and the metal oxide is at least one selected from the group consisting of iron oxide, cobalt oxide, titanium oxide, tin oxide, indium oxide, gallium oxide, zinc oxide, ruthenium oxide, hafnium oxide, and tungsten oxide.

6. The electrode for electrochemical measurement of claim 3, wherein the catalyst is a protein and the protein is at least one selected from enzymes.

7. The electrode for electrochemical measurement of claim 1, wherein the insulator has a volume resistivity value in a range of $1 \times 10^5$ to $1 \times 10^{10}$ Ωcm.

8. The electrode for electrochemical measurement of claim 1, wherein the material for the insulator is selected from the group consisting of polyether ketone, polyketone, polyimide, polycarbonate, polystyrene, and polyethylene.

9. The electrode for electrochemical measurement of claim 1, wherein the catalyst is platinum black.

10. The electrode for electrochemical measurement of claim 1, wherein the cross-linking agent having non-self polymerizability is at least one cross-linking agent having non-self polymerizability selected from the group consisting of polyols, polyamines, polycarboxylic acids, polycarboxylic esters, polycarboxylic halides, polycarbodiimides, and polyisocyanates.

11. An electrode for electrochemical measurement comprising a plurality of carbon nanotubes, a catalyst causing a specific chemical reaction, and an insulator in which the carbon nanotubes and the catalyst are embedded, wherein
the carbon nanotubes are electrically connected with each other by chemical bonding to thereby form a network structure, a part of the catalyst is exposed at a surface of the insulator, and a part of the plurality of the carbon nanotubes are electrically connected to the exposed catalyst to form an electroconductive portion, and
the carbon nanotubes are cross-linked with a cross-linking agent having non-self polymerizability.

12. The electrode for electrochemical measurement of claim 11, wherein a part of the plurality of the carbon nanotubes are exposed through the insulator at plural spots on the surface of the insulator to form the electroconductive portion.

13. The electrode for electrochemical measurement of claim 11, wherein the catalyst is at least one selected from the group consisting of metal, metal oxide, protein,. and carbon pieces carrying any of these substances.

14. The electrode for electrochemical measurement of claim 13, wherein the catalyst is a metal and the metal is at least one selected from the group consisting of platinum, silver, gold, iron, copper, and silicon.

15. The electrode for electrochemical measurement of claim 13, wherein the catalyst is a metal oxide and the metal oxide is at least one selected from the group consisting of iron oxide, cobalt oxide, titanium oxide, tin oxide, indium oxide, gallium oxide, silicon oxide, silicon, zinc oxide, ruthenium oxide, hafnium oxide, and tungsten oxide.

16. The electrode for electrochemical measurement of claim 13, wherein the catalyst is a protein and the protein is at least one selected from enzymes.

17. The electrode for electrochemical measurement of claim 11, wherein the insulator has a volume resistivity value in a range of $1\times10^5$ to $1\times10^{10}$ $\Omega$cm.

18. The electrode for electrochemical measurement of claim 11, wherein the material for the insulator is selected from the group consisting of polyether ketone, polyketone, polyimide, polycarbonate, polystyrene, and polyethylene.

19. The electrode for electrochemical measurement of claim 11, wherein the catalyst is platinum black.

20. The electrode for electrochemical measurement of claim 2, wherein the cross-linking agent having non-self polymerizability is at least one cross-linking agent having non-self polymerizability selected from the group consisting of polyols, polyamines, polycarboxylic acids, polycarboxylic esters, polycarboxylic halides, polycarbodiimides, and polyisocyanates.

* * * * *